(12) United States Patent
DiFrancesco et al.

(10) Patent No.: US 7,938,839 B2
(45) Date of Patent: May 10, 2011

(54) INTERLOCKING TRIGGER ASSEMBLY FOR A SUTURING DEVICE

(75) Inventors: Francis J. DiFrancesco, Foxboro, MA (US); Jerry R. Griffiths, Pembroke, MA (US)

(73) Assignee: Symmetry Medical New Bedford, Inc, New Bedford, MA (US)

( * ) Notice: Subject to any disclaimer, the term of this patent is extended or adjusted under 35 U.S.C. 154(b) by 1495 days.

(21) Appl. No.: 10/788,111

(22) Filed: Feb. 26, 2004

(65) Prior Publication Data

US 2004/0254605 A1 Dec. 16, 2004

Related U.S. Application Data

(60) Provisional application No. 60/478,670, filed on Jun. 13, 2003.

(51) Int. Cl.
*A61B 17/04* (2006.01)
*A61B 17/12* (2006.01)
*A61B 17/00* (2006.01)

(52) U.S. Cl. ...................................... 606/144; 606/205

(58) Field of Classification Search .................. 606/148, 606/147, 144, 205, 208, 139, 172, 145, 146, 606/206, 207
See application file for complete search history.

(56) References Cited

U.S. PATENT DOCUMENTS

| 3,842,840 | A | * | 10/1974 | Schweizer | 606/145 |
| 4,957,498 | A | * | 9/1990 | Caspari et al. | 606/146 |
| 5,257,999 | A | | 11/1993 | Slanetz | |
| 5,458,598 | A | * | 10/1995 | Feinberg et al. | 606/52 |
| 5,735,874 | A | * | 4/1998 | Measamer et al. | 606/208 |
| 5,776,150 | A | * | 7/1998 | Nolan et al. | 606/148 |
| 5,843,099 | A | * | 12/1998 | Nichols et al. | 606/144 |
| 6,533,795 | B1 | * | 3/2003 | Tran et al. | 606/144 |
| 7,101,371 | B2 | * | 9/2006 | Dycus et al. | 606/49 |

* cited by examiner

*Primary Examiner* — Gary Jackson
*Assistant Examiner* — L Bachman
(74) *Attorney, Agent, or Firm* — AKC Patents LLC; Aliki K. Collins (57) ABSTRACT

An endoscopic suturing device having an interlocking trigger assembly for preventing premature needle deployment. The suturing device comprises a handle assembly that includes a movable handle interlocking with a trigger. The suturing device further comprises an end effector having an upper jaw, a lower jaw and a needle/suture mechanism. The motion of the movable handle causes the upper jaw to move relative to the lower jaw. The activation of the trigger causes deployment of the needle/suture mechanism. The interlocking mechanism ensures that the needle/suture is deployed only when the upper jaw is below a maximum allowable distance from the lower jaw.

16 Claims, 10 Drawing Sheets

INTERLOCKING TRIGGER ASSEMBLY FOR A SUTURING DEVICE

CROSS REFERENCE TO RELATED CO-PENDING APPLICATIONS

This application claims the benefit of U.S. provisional application Ser. No. 60/478,670 filed on Jun. 13, 2003 and entitled INTERLOCKING TRIGGER ASSEMBLY FOR A SUTURING DEVICE which is commonly assigned and the contents of which are expressly incorporated herein by reference.

FIELD OF THE INVENTION

The present invention relates to a suturing device, and more particularly to a suturing device with an interlocking trigger assembly.

BACKGROUND OF THE INVENTION

Suturing or stitching of tissue is performed in surgical procedures or other cases where closing of incisions or cuts is required. Suturing is usually performed by grasping the tissue to be sutured, pushing a first end of a needle having a needle tip through one side of the tissue and then grasping the needle tip from the other side of the tissue to pull the needle through. The needle and a suture attached to a second end of the needle are then pulled through the tissue and the suture is tied.

Suturing is a simple procedure when it is performed on external tissues because the needle and suture can be easily manipulated. However, in endoscopic or other minimally invasive surgical procedures that require suturing of internal tissues access to the suturing area is limited and this limits the ability to manipulate the needle and suture.

Figure 4:
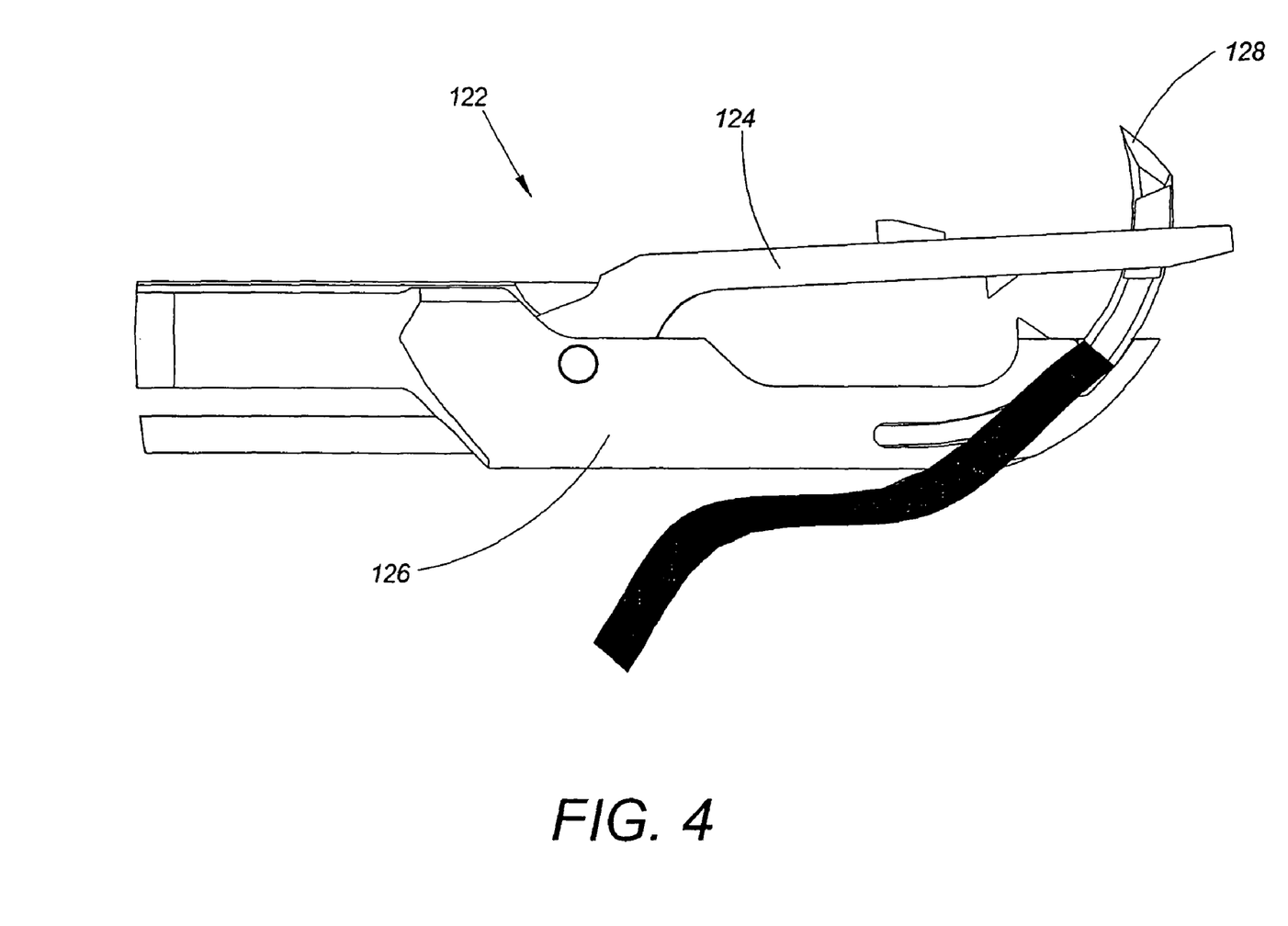
FIG. 4 is a side view of an end effector.

Various types of endoscopic surgical instruments are known in the art that allow suturing and stitching of internal tissues during endoscopic surgical procedures. These instruments generally include a slender tube containing a push rod which is axially movable within the tube by means of a manual actuator. An end effector is coupled to a distal end of the tube and the push rod so that axial movement of the push rod is translated to rotational or pivotal movement of the end effector. Referring to FIG. 4, an end effector 122 that allows suturing of internal tissue usually includes an upper jaw 124 and a lower jaw 126 that grasp the soft tissue and at a predetermined minimum distance between the upper and lower jaw deploy a needle and a suture 128. The needle and suture 128 are pushed from the lower jaw 126 to the upper jaw 124, where the upper jaw captures them and pulls them through the soft tissue. In this prior art suturing devices there is no control of the distance between the upper and lower jaw and of the timing when the needle is deployed. As a result, in some cases, the needle is deployed prematurely, i.e., the needle is engaged in tissue, but not captured by the upper jaw. When premature needle deployment occurs, the suturing action needs to be repeated. Multiple premature needle deployments may results in soft tissue damage. Another problem of premature deployment is that it is difficult to back the needle out once it is into tissue but cannot be captured on the other side. Accordingly there is a need to prevent premature needle deployment in endoscopic suturing devices that utilize a jaw-type end effector for needle manipulation during endoscopic suturing procedures.

SUMMARY OF THE INVENTION

The present invention solves the problem of premature needle deployment in a suturing device by employing an interlocking trigger mechanism. The interlocking trigger mechanism accomplishes this by making the needle deployment trigger action dependent on the position of the jaw actuation handle. When the jaw actuation handle is in its forward position, and therefore the upper jaw is open beyond the maximum deployment position, the needle deployment trigger is blocked from moving by a portion of the jaw actuation handle. The jaw actuation handle is constructed such that once it reaches the proper position, it ceases to block the needle deployment trigger, and allows it to move, effectively interlocking the needle deployment trigger to the jaw actuation handle.

In general, in one aspect, the invention features a surgical instrument comprising a handle assembly having a stationary handle and a movable handle an end effector assembly and a trigger. The movable handle is pivotally connected to the stationary handle. The end effector assembly includes a first member movably connected to a second member and a third member deployable between the first and second members. The movable handle is operably connected to the end effector assembly thereby effectuating motion of the second end effector member relative to the first end effector member. The trigger is operably connected to the third end effector member and is adapted to effectuate deployment of the third end effector member only when a distance between the first and second end effector members is below a maximum allowable distance.

Implementations of this aspect of the invention may include one or more of the following features. The movable handle includes a first handle segment that interlocks with a first trigger segment when the distance between the first and second end effector members is larger than the maximum allowable distance thereby preventing activation of the trigger and accordingly deployment of the third end effector member. The first and second end effector members may be first and second jaws, respectively. The third end effector member may be a needle. The needle may further include a suture. The surgical instrument may further include a suture cartridge. The surgical instrument may further include first actuation means for operably connecting the movable handle to the end effector assembly thereby translating motion of the movable handle to motion of the second end effector member relative to the first end effector member. The surgical instrument may also include second actuation means for operably connecting the trigger to the third end effector member thereby translating trigger activation to deployment of the third end effector member. The handle assembly may also include a ratchet mechanism adapted to secure the movable handle relative to the stationary handle. The movable handle may further include an elongated handle segment extending from the first handle segment and an operator may use the elongated handle segment to move the movable handle relative to the stationary handle. The trigger may also include an elongated trigger segment extending from the first trigger segment and an operator may use the elongated trigger segment to activate the trigger and thereby the third end effector member deployment. The surgical instrument may further include a position indicator adapted to confirm that the distance between the first and second end effector members is below the maximum allowable distance. The position indicator may be an audible signal, an optical signal, a mechanical signal, a vibration signal, or a tactile feel. The maximum allowable distance between the first and second end effector members for the deployment of the third end effector member may be in the range between 0.5 and 0.01 inch. In one case the maximum allowable distance is 0.145 inch. The end effector assembly may be partially or entirely disposable.

In general, in another aspect, the invention features a handle for a surgical instrument comprising a stationary handle, a movable handle and a trigger. The movable handle is pivotally connected to the stationary handle and includes a first handle segment. The trigger is operably connected to an end effector member and includes a first trigger segment. The first trigger segment interlocks with the first handle segment thereby preventing activation of the trigger and deployment of the end effector member when a distance between the movable handle and the stationary handle is larger than a maximum allowable distance.

In general, in another aspect, the invention features in a surgical instrument having an end effector assembly, a method for controlling deployment of a first end effector member of the end effector assembly. The method includes providing a stationary handle, providing a movable handle pivotally connected to the stationary handle and operably connected to the end effector assembly thereby translating motion of the movable handle to motion of a second end effector member of the end effector assembly relative to a third end effector member of the end effector assembly, and finally providing a trigger being operably connected to the first end effector member and comprising a first trigger segment and wherein the first trigger segment interlocks with a first handle segment of the movable handle thereby preventing activation of the trigger and deployment of the first end effector member when a distance between the second end effector member and the third end effector member is larger than a maximum allowable distance.

Among the advantages of this invention may be one or more of the following. The interlocking mechanism ensures that the needle/suture is deployed only when the upper jaw is below a maximum allowable distance from the lower jaw. This prevents premature needle deployment and thereby soft tissue damage from multiple unsuccessful attempts.

The details of one or more embodiments of the invention are set forth in the accompanying drawings and description below. Other features, objects and advantages of the invention will be apparent from the following description of the preferred embodiments, the drawings and from the claims.

BRIEF DESCRIPTION OF THE DRAWINGS

Referring to the figures, wherein like numerals represent like parts throughout the several views.

DETAILED DESCRIPTION OF THE INVENTION

Figure 1A:
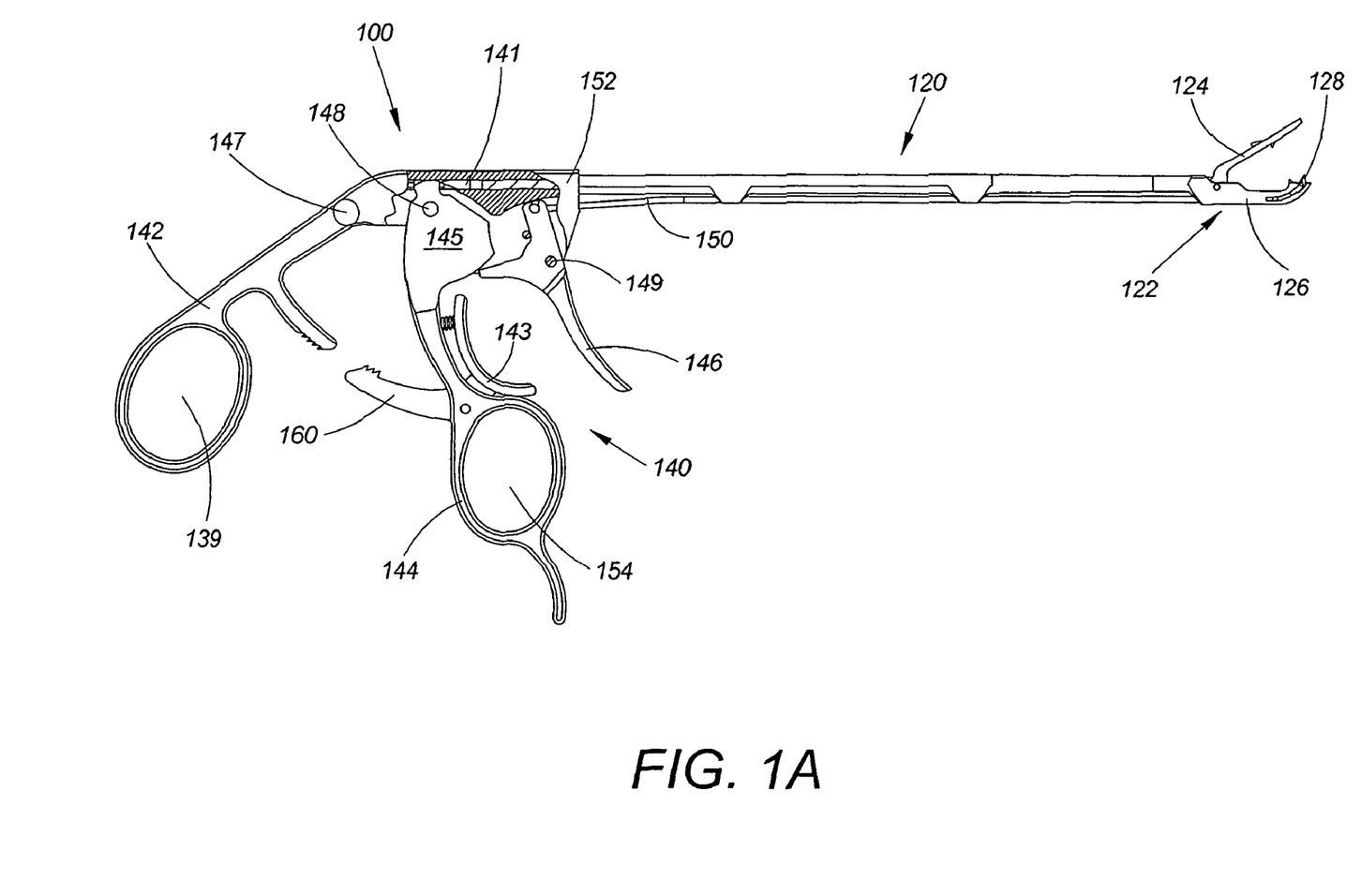
FIG. 1A is a side view of the endoscopic instrument with the front end assembly jaws open beyond the maximum distance for needle deployment.
Figure 1B:
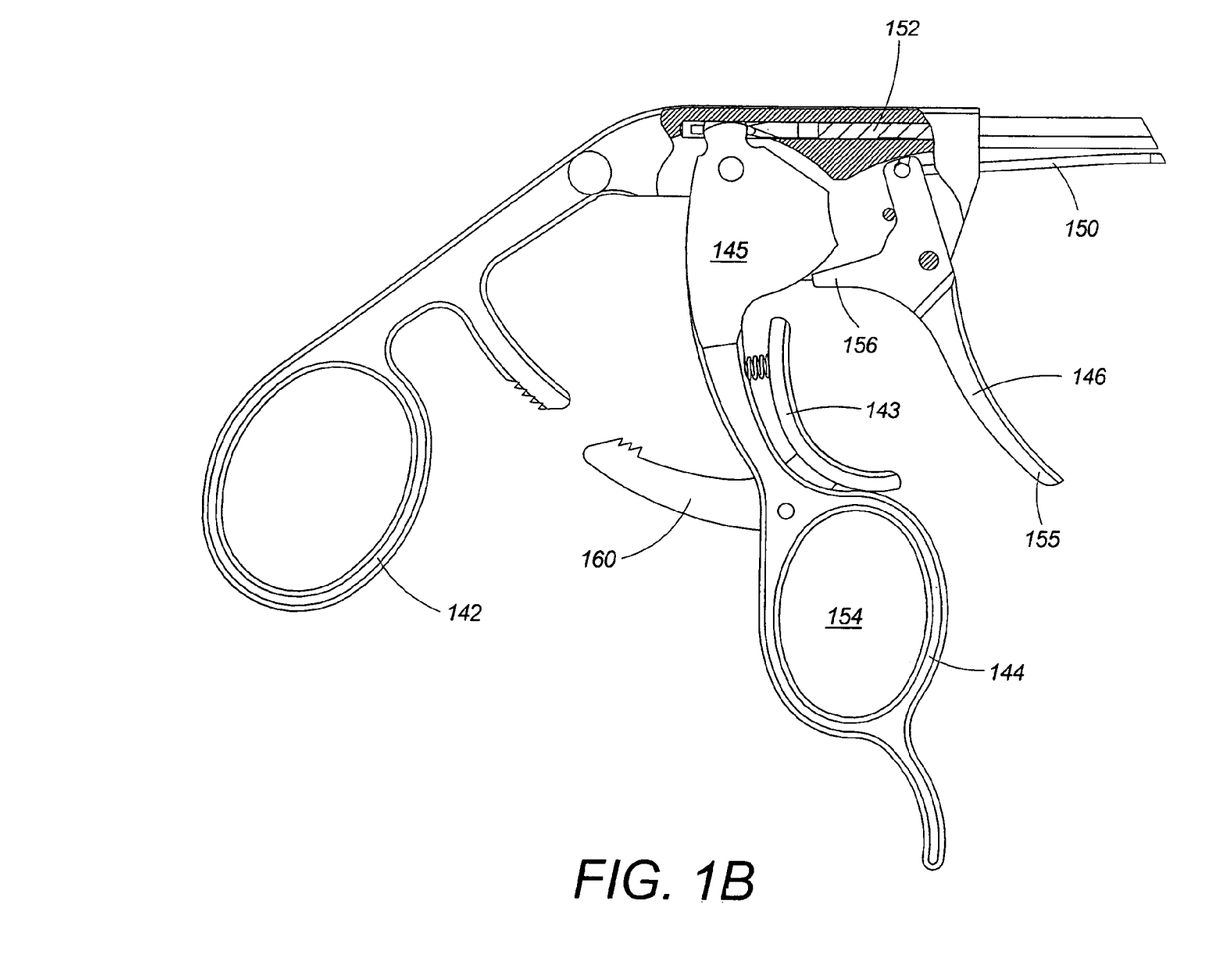
FIG. 1B is a partial cross-sectional view of the handle assembly of FIG. 1A.
Figure 1C:
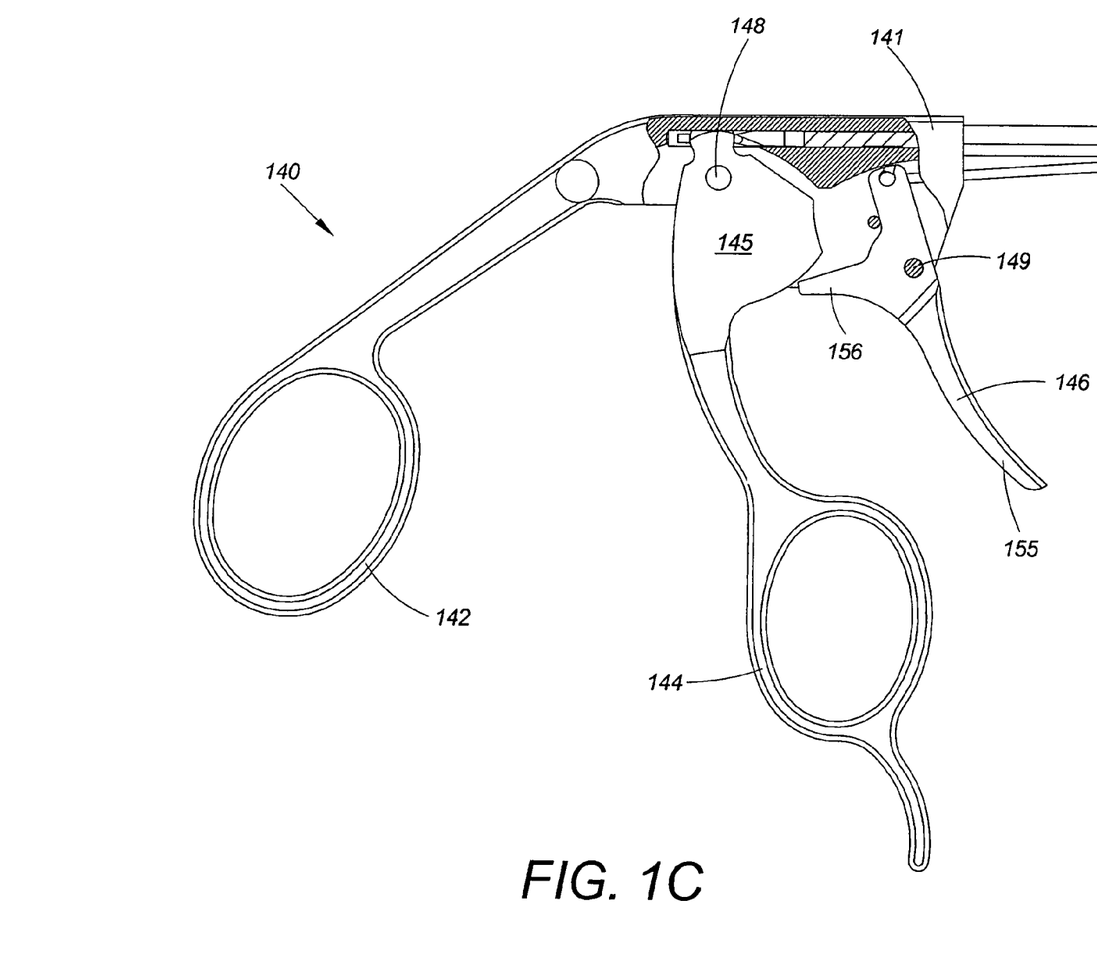
FIG. 1C is a partial cross-sectional view of another embodiment of the handle assembly of FIG. 1A.

Referring to FIG. 1A, the endoscopic instrument 100 includes a front end assembly 120 with an end effector 122, and a handle assembly 140. The end effector 122 includes a movable upper jaw 124, a lower jaw, 126 and a needle/suture mechanism 128. The handle assembly 140 includes a stationary handle 142, a movable handle 144, a trigger 146 and a base 141, also shown in FIG. 1B and FIG. 1C. Stationary handle 142 is attached to the base 141 and movable handle 144 and trigger 146 are pivotally attached to the base 141 via pivot mechanisms 148 and 149, respectively. In the embodiment of FIG. 1B movable handle 144 is secured at a predetermined distance relative to the stationary handle 142 via a ratchet mechanism 160. Movable handle 144 is further connected to the movable upper jaw 124 via an actuator rod 152. Actuator rod 152 translates the motion of the movable handle 144 into a motion of the upper jaw 124. Trigger 146 is further connected to the needle/suture mechanism 128 via a second actuator rod 150. Actuator rod 150 translates the trigger motion into deployment of the needle/suture mechanism 128. Movable handle 144 includes a finger loop 154, a finger rest 143, and an upper segment 145. Upper segment 145 has a shape appropriate for preventing the motion of the trigger 146, and therefore needle/suture 128 deployment, when the upper jaw 124 is beyond the allowable maximum distance from the lower jaw 122 for a successful needle deployment. Trigger 146 includes a downward extending segment 155 and a horizontally extending segment 156. The horizontally extending segment 156 interlocks with the upper segment 145 of the movable handle 144, when the jaws 124 and 126 are open and the distance between them is beyond a maximum allowable distance for achieving a successful needle/suture 128 deployment. The downward extending segment 155 is used to move the trigger 146 with a finger (not shown). Stationary handle 142 includes a finger loop 139 and a suture wrapping mechanism 147.

Figure 2A:
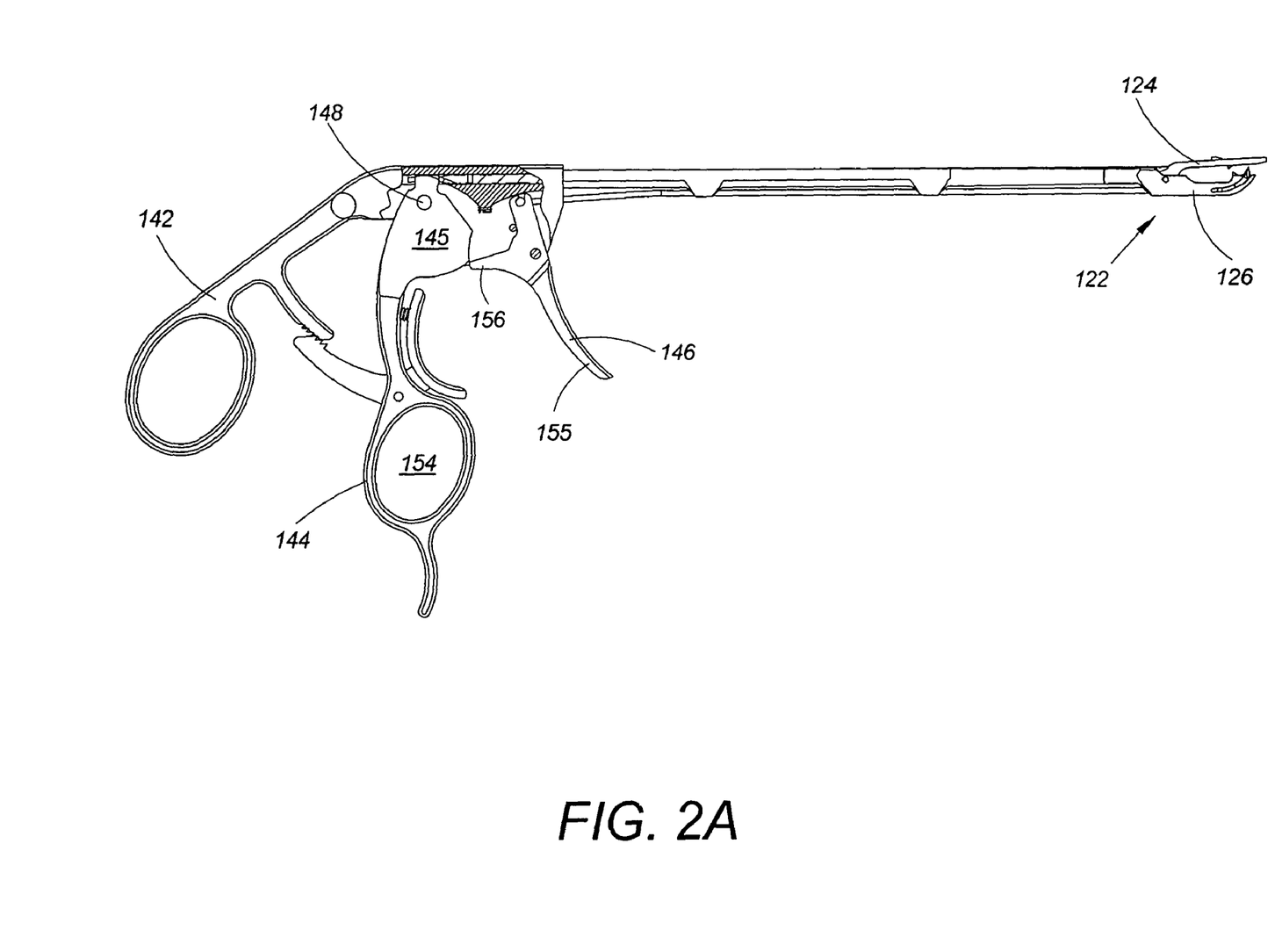
FIG. 2A is a side view of the endoscopic instrument with the front end assembly jaws open at the maximum distance for needle deployment position.
Figure 2B:
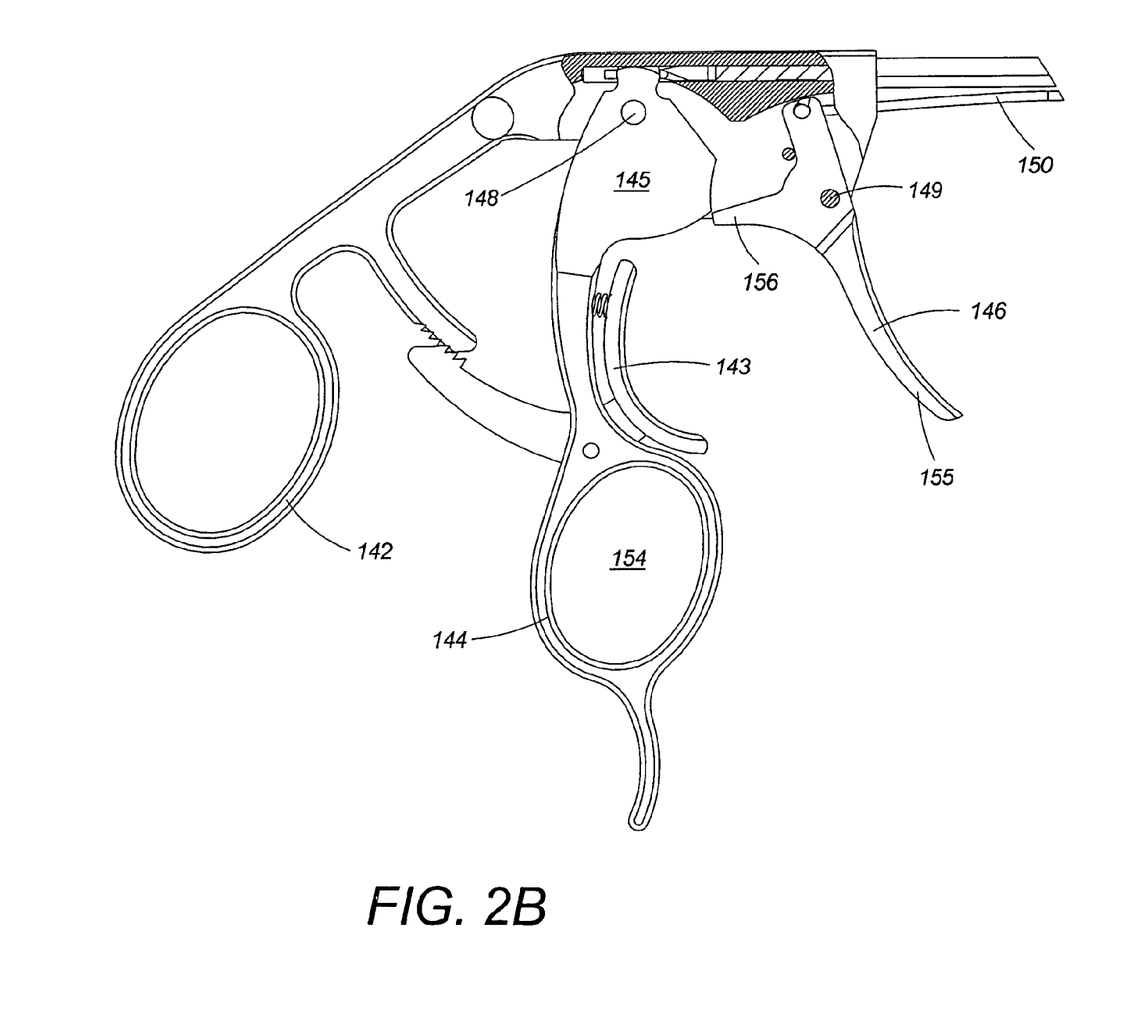
FIG. 2B is a partial cross-sectional view of the handle assembly of FIG. 2A.
Figure 2C:
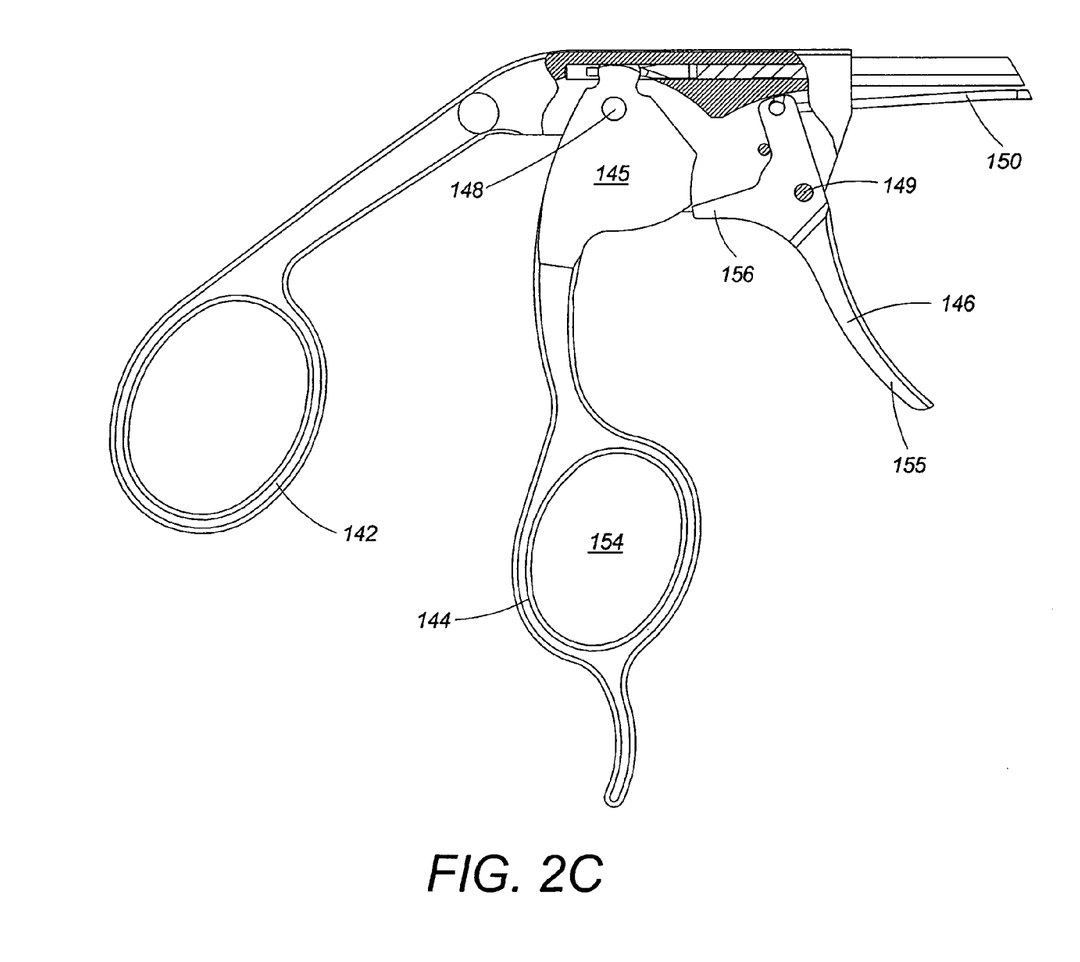
FIG. 2C is a partial cross-sectional view of another embodiment of the handle assembly of FIG. 2A.

Referring to FIG. 2A, an operator moves the handle 144 closer to the stationary handle 142, by placing his finger inside the finger loop 154 and pivoting the handle 144 around the pivot point 148 clockwise. This pivoting motion of the handle 144 towards the stationary handle 142 causes the upper jaw 124 of the end effector 122 to move closer to the lower jaw 126. At the point where the distance between the upper jaw 124 and the lower jaw 126 reaches the maximum allowable for achieving a successful needle/suture 128 deployment the upper segment 145 of the handle 144 disengages from the horizontally extending segment 156 of the trigger 146, as shown in FIG. 2B and FIG. 2C. At this point the operator can activate the trigger 146 by pushing the downward extending segment 155 with his finger towards the movable handle 144, thereby causing the trigger 146 to pivot around pivot point 149 clockwise and to deploy the needle/suture mechanism 128 via the actuator rod 150. In the embodiment of FIG. 2B the position of the movable handle 144 is secured to the stationary handle 142 via the ratchet mechanism 160. An audible signal confirms the ratchet engagement and the securing of the movable handle 144 position relative to the stationary handle 142. The operator can now safely activate the trigger 146 causing the deployment of the needle/suture mechanism 128.

Figure 3A:
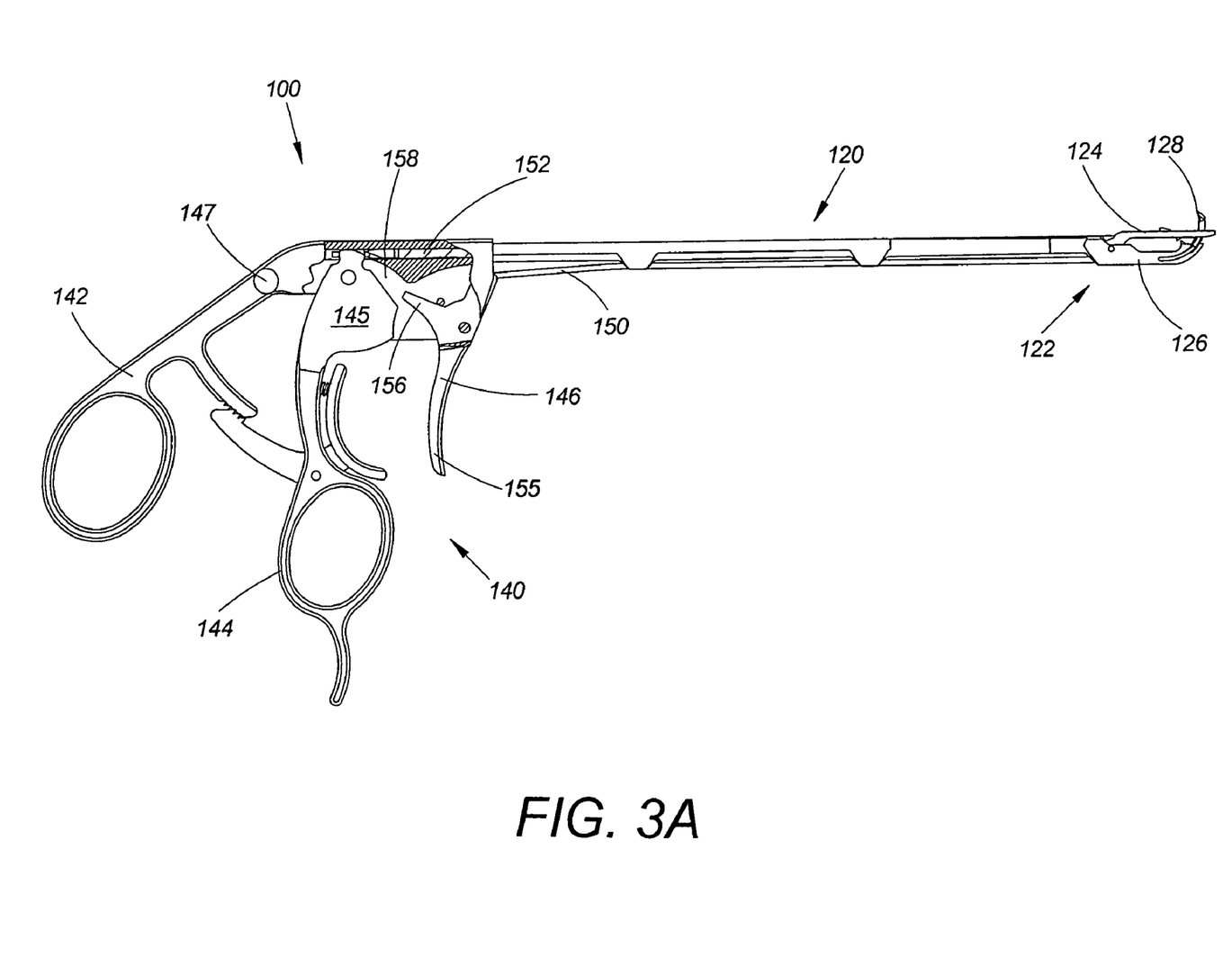
FIG. 3A is a side view of the endoscopic instrument with the front end assembly jaws closed and the needle deployed.
Figure 3B:
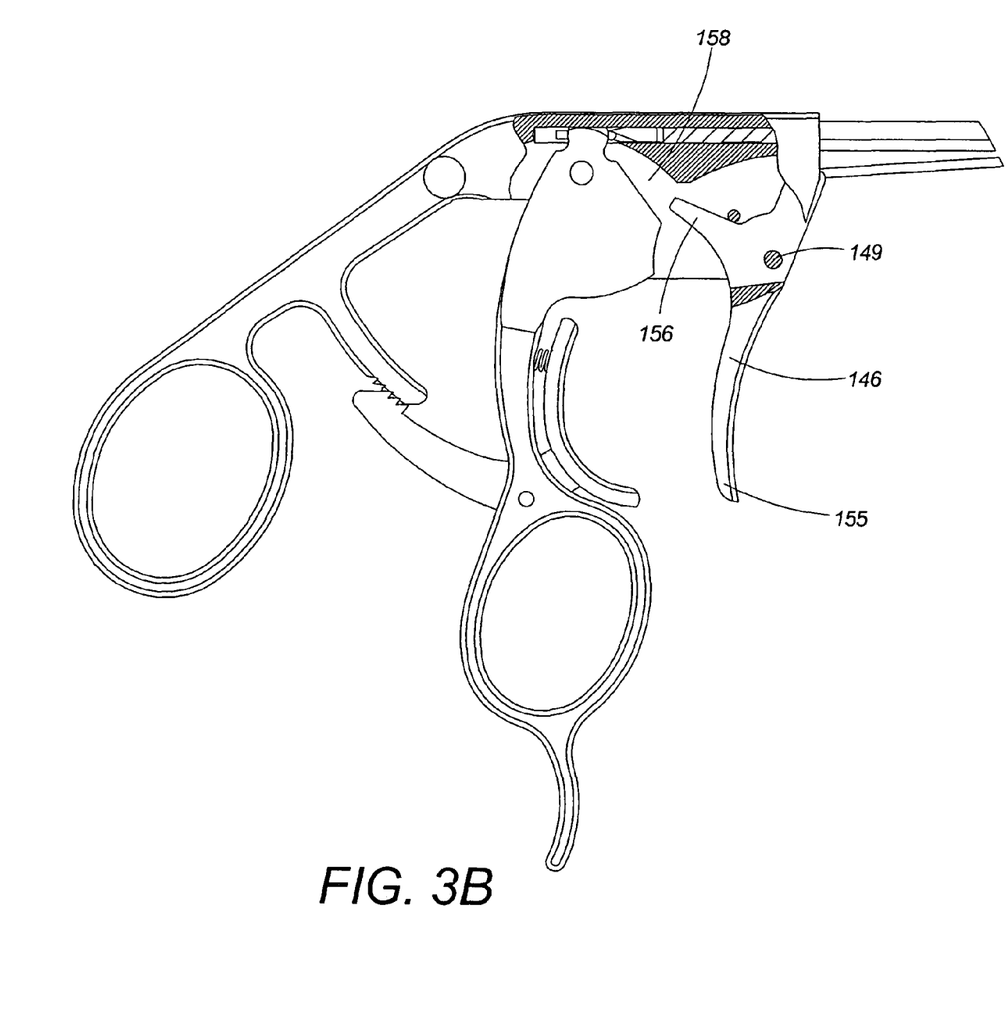
FIG. 3B is a partial cross-sectional view of the handle assembly of FIG. 3A.
Figure 3C:
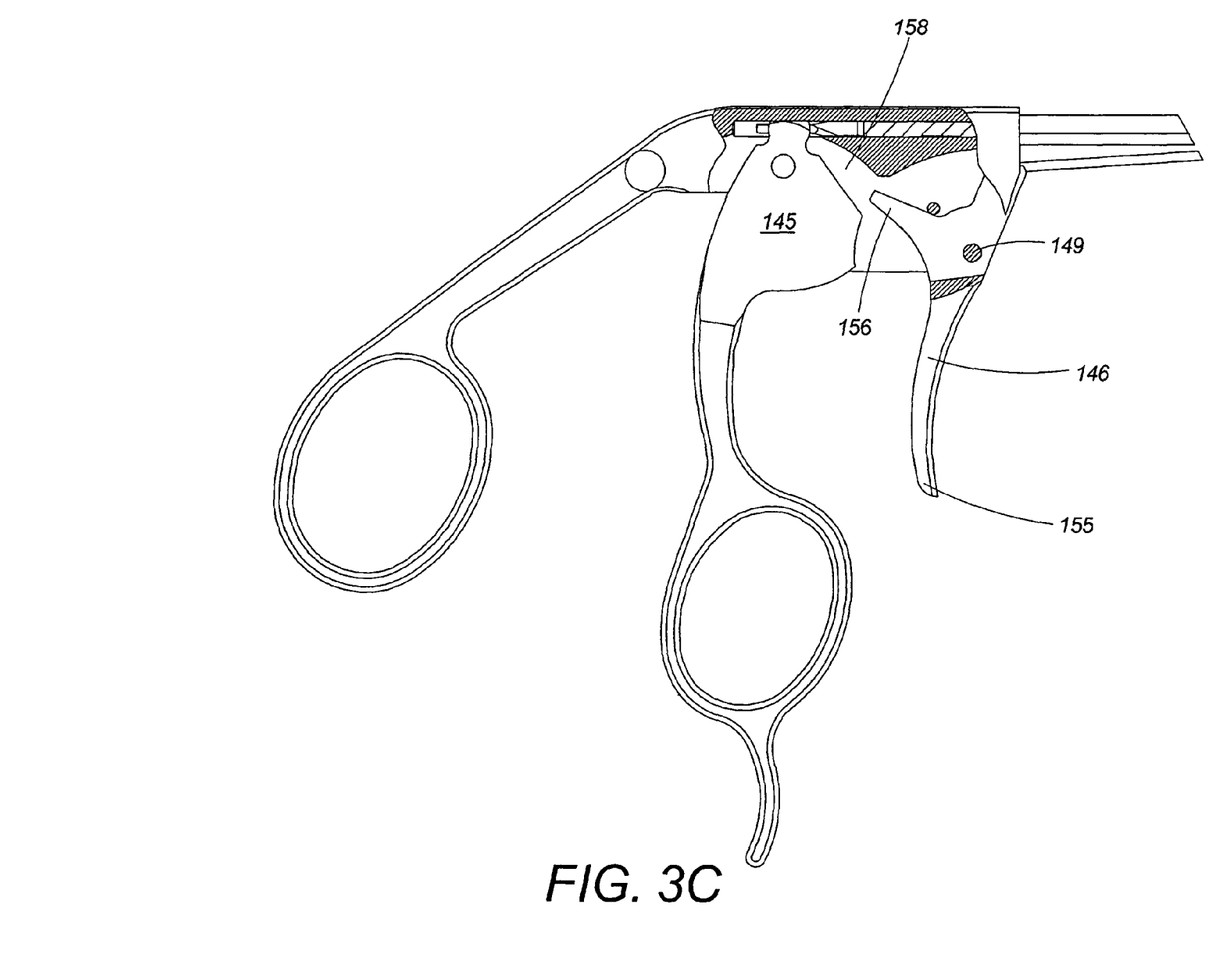
FIG. 3C is a partial cross-sectional view of another embodiment of the handle assembly of FIG. 3A.

Referring to FIG. 3A, the operator activated the trigger 146 causing deployment of the needle/suture mechanism 128. The trigger 146 pivots around pivot point 149 and the horizontally extending segment 155 moves freely beyond the upper segment 145 of the movable handle 144 in the space 158. At this point the upper and lower jaws, 124, and 126, respectively, are fully closed.

In the next step the operator pivots the trigger 146 counter clockwise away from the movable handle 144, then pivots the movable handle 144 counter clockwise away from the stationary handle 142, thereby causing the jaws 124, 126 to open and the needle/suture mechanism 128 to disengage, bringing the instrument back in the position of FIG. 1A.

In one example, the maximum distance between the upper jaw and the lower jaw where needle/suture deployment can safely occur is 0.145 inches. Typical dimensions for the jaws are 0.500×0.175 inches. Typical dimensions for the handles are 0.230×4.5×1.75 inches. Typical dimensions for the trigger are 0.230×0.750×1.800 inches. The endoscopic instrument may be made of various types of biocompatible stainless steels, ceramics, plastics, or composites. The suture may be made of biocompatible material, Nylon, Dacron, Polypropylene, or other materials commonly used for anchoring soft tissue to bone. The end effector may be disposable or non-disposable and may be made of various types of biocompatible stainless steels, metals, alloys, composites and plastics.

Several embodiments of the present invention have been described. Nevertheless, it will be understood that various modifications may be made without departing from the spirit and scope of the invention. Accordingly, other embodiments are within the scope of the following claims.

What is claimed is:

1. A surgical suturing instrument comprising:
    a handle assembly comprising a stationary handle and a movable handle pivotally connected to said stationary handle;
    an end effector assembly comprising a first jaw member movably connected to a second jaw member and a needle deployable from said first jaw member and configured to be captured by said second jaw member and wherein said movable handle is operably connected to said second jaw member, so as to effectuate motion of said second jaw member relative to said first jaw member; and
    a trigger operably connected to said needle and being adapted to effectuate deployment of said needle from said first jaw member and capturing of said needle by said second jaw member when said first and second jaw members are open and spaced apart relative to each other by a distance dimensioned to be below a maximum allowable distance.

2. The surgical suturing instrument of claim 1 wherein said movable handle comprises a first handle segment, said trigger comprises a first trigger segment, and wherein said first trigger segment interlocks with said first handle segment when said distance between said first and second jaw members is larger than said maximum allowable distance thereby preventing activation of said trigger and accordingly deployment of said needle.

3. The surgical suturing instrument of claim 2 wherein said movable handle further comprises an elongated handle segment extending from said first handle segment and wherein an operator uses said elongated handle segment to move said movable handle relative to said stationary handle.

4. The surgical suturing instrument of claim 2 wherein said trigger further comprises an elongated trigger segment extending from said first trigger segment and wherein an operator uses said elongated trigger segment to activate said trigger.

5. The surgical suturing instrument of claim 1 wherein said needle further comprises a suture.

6. The surgical suturing instrument of claim 5 further comprising a suture cartridge.

7. The surgical instrument of claim 1 further comprising first actuation means for operably connecting said movable handle to said second jaw member thereby translating motion of said movable handle to motion of said second jaw member relative to said first jaw member.

8. The surgical suturing instrument of claim 1 further comprising second actuation means for operably connecting said trigger to said needle thereby translating trigger activation to deployment of said needle.

9. The surgical suturing instrument of claim 1 wherein said handle assembly further comprises a ratchet mechanism adapted to secure said movable handle relative to said stationary handle.

10. The surgical suturing instrument of claim 1 further comprising a position indicator adapted to confirm that said distance between said first and second end effector members is below the maximum allowable distance.

11. The surgical suturing instrument of claim 10 wherein said position indicator comprises any of audible signals, mechanical signals, vibration signals, or tactile feel.

12. The surgical suturing instrument of claim 1 wherein said maximum allowable distance is in the range between 0.5 and 0.01 inch.

13. The surgical suturing instrument of claim 1 wherein said maximum allowable distance is 0.145 inch.

14. The surgical suturing instrument of claim 1 wherein said end effector assembly is partially or entirely disposable.

15. A surgical suturing instrument comprising:
    a handle assembly comprising a stationary handle and a movable handle pivotally connected to said stationary handle;
    an end effector assembly comprising a first jaw member movably connected to a second jaw member and a needle deployable from said first jaw member and configured to be captured by said second jaw member and wherein said movable handle is operably connected to said second jaw member, so as to effectuate motion of said second jaw member relative to said first jaw member;
    a trigger operably connected to said needle and being adapted to effectuate deployment of said needle from said first jaw member and capturing of said needle by said second jaw member when said first and second jaw members are open and spaced apart relative to each other by a distance dimensioned to be below a maximum allowable distance;
    a position indicator adapted to confirm that said distance between said first and second jaw members is below the maximum allowable distance; and
    wherein said position indicator comprises any of an audible signal, mechanical signal, optical signal, vibration signal or tactile feel signal.

16. A method for controlling deployment of a needle member of an end effector assembly comprising:
    providing a stationary handle;
    providing a movable handle pivotally connected to said stationary handle and operably connected to a first jaw member of said end effector assembly thereby translating motion of said movable handle to motion of said first jaw member of said end effector assembly relative to a second jaw member of said end effector assembly; and
    providing a trigger being operably connected to said needle member and comprising a first trigger segment and wherein said first trigger segment interlocks with a first handle segment of said movable handle thereby preventing activation of said trigger and deployment of said needle member when a distance between said first jaw member and said second member is larger than a maximum allowable distance; and deploying said needle from said first jaw member via said trigger and capturing said needle by said second jaw member when said first and second jaw members are open and spaced apart relative to each other by said distance dimensioned to be below said maximum allowable distance.

* * * * *